United States Patent [19] [11] 4,123,613
Bernardi et al. [45] Oct. 31, 1978

[54] SUBSTITUTED PYRAZINES AS INHIBITORS OF PLATELET AGGREGATION

[75] Inventors: Luigi Bernardi; Carlo Elli; Giovanni B. Falconi, all of Milan; Rosella Ferrari, Sovico (Milan), all of Italy

[73] Assignee: Societá Farmaceutici Italia S.p.A., Milan, Italy

[21] Appl. No.: 799,167

[22] Filed: May 23, 1977

[30] Foreign Application Priority Data

May 26, 1976 [GB] United Kingdom ............... 21801/76

[51] Int. Cl.² .......................................... C07D 241/18
[52] U.S. Cl. .................................. 544/408; 260/285.5; 424/250; 424/261; 544/336; 544/409
[58] Field of Search ........... 260/250 BN, 250 B, 285.5

[56] References Cited

U.S. PATENT DOCUMENTS

| 3,238,211 | 3/1966 | Camerino et al. | 260/285.5 |
| 3,901,894 | 8/1975 | Kornfeld et al. | 260/285.5 |
| 3,996,228 | 12/1976 | Arcari et al. | 260/256.4 C |
| 4,004,011 | 1/1977 | Hauth et al. | 424/261 |

Primary Examiner—Donald G. Daus
Assistant Examiner—Lisa Jones
Attorney, Agent, or Firm—Stevens, Davis, Miller & Mosher

[57] ABSTRACT

Novel substituted pyrazine derivatives are disclosed having the general formula (I):

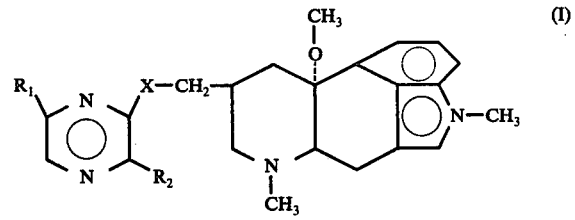

where $R_1$ and $R_2$ may be methyl, methoxy, halogen (particularly chlorine, bromine or fluorine), or hydrogen, with the proviso that $R_1$ and $R_2$ cannot both be hydrogen, and X may be S or NH.

These novel substituted pyrazine derivatives show a remarkable activity as inhibitors of platelet aggregation at very low dosages.

6 Claims, No Drawings

SUBSTITUTED PYRAZINES AS INHIBITORS OF PLATELET AGGREGATION

The present invention relates to novel substituted pyrazine derivatives of the general formula (I):

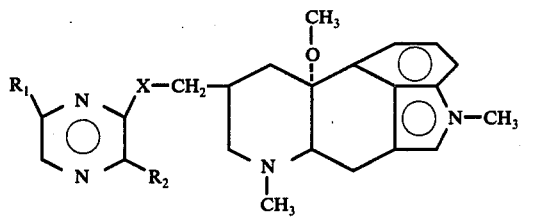

where $R_1$ and $R_2$ may be methyl, methoxy, halogen (particularly chlorine, bromine or fluorine), or hydrogen, with the proviso that $R_1$ and $R_2$ cannot both be hydrogen, and
X may be S or NH.

These novel substituted pyrazine derivatives show a remarkable activity as inhibitors of platelet aggregation at very low dosages, and this activity is even more unexpected and surprising since it is not present in the unsubstituted parent compound, i.e., where $R_1 = R_2 =$ H.

The novel substituted pyrazine derivatives of the present invention are prepared by condensing 10-methoxy-1,6-dimethylergoline-8β-methanol tosylate (prepared from 10-methoxy-1,6-dimethylergoline-8β-methanol and tosyl chloride) with the sodium salt of an appropriate mercaptopyrazine or aminopyrazine in an inert solvent and at a temperature of 50° to 100° C.

The new products are insoluble in water but they can be easily solubilized by the addition of one mol of tartaric acid. In the biological tests hereafter described, the products were assayed as the tartrate salts.

For the study on the platelet aggregation "in vitro", the turbidimetric method initially described by Born and Cross (J. Physiol. 168, 178, 1963) was employed but with some changes, principally due to the use of rabbit platelets, rather than human or pig platelets as reported in the original method:

(1) Preparation of platelet-rich plasma (PRP) and platelet-poor plasma (PPP).

Male rabbits weighing 2.5–3.5 Kg were used. Fifty four ml of blood were withdrawn from the carotid artery of rabbits anaesthetized with ether. The blood was gently mixed with six ml of 3.8% trisodium citrate as anticoagulant.

The PRP was obtained by centrifugation at 400 g for 10 minutes. The concentration of the platelets was adjusted to 250,000/mm³ by diluting the PRP with PPP prepared by a second centrifugation of the blood samples for about 10 minutes at 2000 g.

The aggregation experiments were generally performed within 1–2 h from the time of blood collection.

(2) ADP-induced platelet aggregation

In the cuvette of the aggregometer, reagents were added as follows: 0.8 ml drug solution or saline, and 0.2 ml ADP, at the molar concentration of $2.2 \times 10^{-4}$. The turbidimetry was checked after 1½, 3 and 6 minutes. The inhibition of the aggregation is given in the table below as percent of ADP controls at the three times.

Generally, four concentrations of test compounds were employed in the following decreasing order: 200, 100, 50, 25 mcg/ml.

As reported in the table below, the unsubstituted pyrazine derivatives (355/895 and 355/917) show a very low activity at all three times whereas the substituted pyrazines and in particular compounds 355/900, 355/915, 355/918 show a very strong activity at all three times with an $ED_{50}$ in the range of 55–70 mcg/ml. The strong anti-aggregating activity of these compounds makes possible their application in the therapy of vascular diseases such as cerebral and myocardial ischemias of thrombotic origin.

Table

Percent inhibition of platelets aggregation at various times after ADP ($2.2 \times 10^{-4}$).

| Compound | $R_1$ | $R_2$ | X | 200 | 100 | 50 | 25 | time seconds |
|---|---|---|---|---|---|---|---|---|
| 355/895 | H | H | NH | 50 | 10 | — | — | 90 |
| 355/898 | H | Cl | NH | 77 | 67 | 35 | 17 | 90 |
| 355/899 | H | OCH₃ | NH | 60 | 30 | 10 | — | 90 |
| 355/900 | Cl | H | NH | 100 | 80 | 40 | 10 | 90 |
| 355/917 | H | H | S | 15 | — | — | — | 90 |
| 355/915 | H | Cl | S | 100 | 75 | 20 | 10 | 90 |
| 355/918 | OCH₃ | H | S | 100 | 80 | 45 | 25 | 90 |
| 355/895 | H | H | NH | 55 | 12 | — | — | 180 |
| 355/898 | H | Cl | NH | 82 | 71 | 31 | 20 | 180 |
| 355/899 | H | OCH₃ | NH | 61 | 30 | 9 | — | 180 |
| 355/900 | Cl | H | NH | 100 | 70 | 25 | 10 | 180 |
| 355/917 | H | H | S | 12 | — | — | — | 180 |
| 355/915 | H | Cl | S | 100 | 75 | 15 | 10 | 180 |
| 355/918 | OCH₃ | H | S | 100 | 70 | 31 | 20 | 180 |
| 355/895 | H | H | NH | 62 | 20 | 5 | — | 360 |
| 355/898 | H | Cl | NH | 83 | 76 | 45 | 30 | 360 |
| 355/899 | H | OCH₃ | NH | 61 | 30 | 10 | — | 360 |
| 355/900 | Cl | H | NH | 100 | 80 | 30 | 10 | 360 |
| 355/917 | H | H | S | 35 | 10 | — | — | 360 |
| 355/915 | H | Cl | S | 100 | 80 | 25 | 10 | 360 |
| 355/918 | OCH₃ | H | S | 100 | 80 | 42 | 26 | 360 |

The following examples serve to illustrate the invention without however limiting it.

EXAMPLE 1

2-(10'methoxy-1',6'-dimethylergoline-8'β-methyl)amino-3-chloropyrazine (I; $R_1$=H; $R_2$=Cl; X=NH) (355/898).

A mixture of 10 g of 10-methoxy-1,6-dimethylergoline-8β-methanol, 12.4 ml of triethylamine, and 12.6 g of tosyl chloride in 200 ml of methylene chloride is refluxed 5 hr. The solution is washed first with 10% Na₂CO₃ and then with water, the solvent is evaporated in vacuo, and the residue is crystallized from methanol to give 11 g of 10-methoxy-1,6-dimethylergoline-8β-methanol tosylate; m.p. 169° C.

To 860 mg of 3-chloro-2-aminopyrazine in 30 ml of dimethylformamide, 290 mg of NaH 60% suspension are added. The solution is kept at 50° C. for 1 hr, then 1.5 g of 10-methoxy-1,6-dimethylergoline-8β-methanol tosylate are added, and the solution is kept at 50° C. for 3 hr. The solvent is evaporated in vacuo, the residue is washed with pentane, and then dissolved in chloroform. The chloroform solution is washed with water and the solvent evaporated in vacuo. The residue is crystallized from acetone to give 800 mg of 2-(10'-methoxy-1',6'-dimethylergoline-8'β-methyl)amino-3-chloropyrazine; m.p. 148°–149° C.

EXAMPLE 2

2-(10'-methoxy-1',6'-dimethylergoline-8'β-methyl)aminopyrazine (I; $R_1=R_2=H$; $X=NH$) (355/895).

Operating as in Example 1, but employing 2-aminopyrazine, 2-(10'-methoxy-1',6'-dimethylergoline-8'β-methyl)aminopyrazine, m.p. 230° C., is obtained.

EXAMPLE 3

2-(10'-methoxy-1',6'-dimethylergoline-8'β-methyl)amino-3-methoxypyrazine (I; $R_1=H$; $R_2=OCH_3$; $Y=NH$) (355/899).

Operating as in Example 1, but employing 2-amino-3-methoxypyrazine, 2-(10'-methoxy-1',6'-dimethylergoline-8'β-methyl)amino-3-methoxy-pyrazine, m.p. 159° C., is obtained.

EXAMPLE 4

2-(10'-methoxy-1',6'-dimethylergoline-8'β-methyl)amino-6-chloropyrazine (I; $R_1=Cl$; $R_2=H$; $X=NH$) (355/900).

Operating as in Example 1, but employing 2-amino-6-chloropyrazine, 2-(10'-methoxy-1',6'-dimethylergoline-8'β-methyl)amino-6-chloropyrazine, m.p. 155° C., is obtained.

EXAMPLE 5

2-(10'-methoxy-1',6'-dimethylergoline-8'β-methyl)thio-3-methoxypyrazine (I; $R_1=H$; $R_2=OCH_3$; $X=S$) (355/918).

To 750 mg of 2-mercapto-3-methoxypyrazine in 10 ml of methanol, one equivalent of sodium methylate is added. The solution is evaporated in vacuo and the residue taken up in 30 ml of dimethylsulfoxide.

1.8 g of 10-methoxy-1,6-dimethylergoline-8β-methanol tosylate are added and the solution is kept at 80° C. for 90 min. The solvent is evaporated in vacuo and the residue chromatographed on alumina to give, by elution with benezene-ethyl ether, 900 mg of 2-(10'-methoxy-1',6'-dimethylergoline-8'β-methyl)thio-3-methoxypyrazine; m.p. 55° C.

EXAMPLE 6

2-(10'-methoxy-1',6'-dimethylergoline-8'β-methyl)thiopyrazine (I; $R_1=R_2=H$; $X=S$) (355/917).

Operating as in Example 5, but employing 2-mercaptopyrazine, 2-(10'-methoxy-1',6'-dimethylergoline-8'β-methyl)thiopyrazine, m.p. 165° C., is obtained.

EXAMPLE 7

2-(10'-methoxy-1',6'-dimethylergoline-8'β-methyl)thio-3-chloropyrazine (I; $R_1=H$; $R_2=Cl$; $X=S$) (355/915).

Operating as in Example 5, but employing 2-mercapto-3-chloropyrazine, 2-(10'-methoxy-1',6'-dimethylergoline-8'β-methyl)thio-3-chloropyrazine, m.p. 78° C., is obtained.

What is claimed is:

1. A compound having the formula (I):

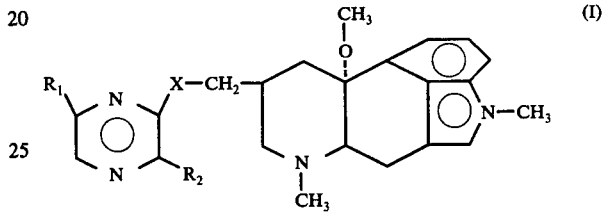

where $R_1$ and $R_2$ may be methyl, methoxy, halogen (particularly chlorine, bromine or fluorine), or hydrogen, with the proviso that $R_1$ and $R_2$ cannot both be hydrogen, and X may be S or NH.

2. A compound as defined in claim 1, which is 2-(10'-Methoxy-1',6'-dimethylergoline-8'β-methyl)amino-3-chloropyrazine.

3. A compound as defined in claim 1, which is 2-(10'-Methoxy-1',6'-dimethylergoline-8'β-methyl)amino-3-methoxy pyrazine.

4. A compound as defined in claim 1, which is 2-(10'-Methoxy-1',6'-dimethylergoline-8'β-methyl)amino-6-chloropyrazine.

5. A compound as defined in claim 1, which is 2-(10'-Methoxy-1',6'-dimethylergoline-8'β-methyl)-thio-3-methoxy-pyrazine.

6. A compound as defined in claim 1, which is 2-(10'-Methoxy-1',6'-dimethylergoline-8'β-methyl)thio-3-chloro-pyrazine.

* * * * *